United States Patent
Aasen

(10) Patent No.: US 10,245,004 B2
(45) Date of Patent: Apr. 2, 2019

(54) SYSTEMS AND METHODS FOR IMBALANCE MEASUREMENT OF ROTATING MACHINERY

(71) Applicant: General Electric Company, Schenectady, NY (US)

(72) Inventor: Eric Christopher Aasen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 14/989,416

(22) Filed: Jan. 6, 2016

(65) Prior Publication Data

US 2017/0188988 A1 Jul. 6, 2017

(51) Int. Cl.
*A61B 6/00* (2006.01)
*A61B 6/03* (2006.01)
*G01M 1/16* (2006.01)
*G01H 1/00* (2006.01)

(52) U.S. Cl.
CPC ............. *A61B 6/586* (2013.01); *A61B 6/032* (2013.01); *A61B 6/035* (2013.01); *A61B 6/4435* (2013.01); *G01H 1/003* (2013.01); *G01M 1/16* (2013.01)

(58) Field of Classification Search
CPC ......... A61B 6/035; A61B 6/586; G01H 1/003
See application file for complete search history.

(56) References Cited

U.S. PATENT DOCUMENTS

| | | | |
|---|---|---|---|
| 5,432,339 A | 7/1995 | Gordon et al. | |
| 5,445,028 A | 8/1995 | Bianchi et al. | |
| 5,448,608 A | 9/1995 | Swain et al. | |
| 5,627,762 A | 5/1997 | Cameron et al. | |
| 6,230,566 B1 | 5/2001 | Lee et al. | |
| 6,412,345 B1 | 7/2002 | Murry et al. | |
| 6,590,960 B2 | 7/2003 | Kroener et al. | |
| 6,748,806 B2 | 6/2004 | Halsmer | |
| 6,890,100 B2 | 5/2005 | Reznicek et al. | |
| 7,650,252 B2 | 1/2010 | Douglas | |
| 8,532,899 B1 | 9/2013 | Loomis | |

(Continued)

FOREIGN PATENT DOCUMENTS

JP 2007-000606 A 1/2007

OTHER PUBLICATIONS

Extended European Search Report and Opinion issued in connection with corresponding EP Application No. 16161970.5 dated May 19, 2017.

*Primary Examiner* — Dani Fox
(74) *Attorney, Agent, or Firm* — Dean D. Small; The Small Patent Law Group, LLC

(57) ABSTRACT

A balancing system for use with a rotating member disposed in a stationary housing is configured for mounting to the stationary housing, and includes a first inclinometer and at least one processor. The first inclinometer is configured to provide inclination information at a first frequency, and to provide vibration information at a second frequency. The second frequency is higher than the first frequency. The at least one processor is operably coupled to the first inclinometer to acquire the vibration information. The at least one processor is configured to determine a state of balance of the rotating member using the vibration information but not the inclination information.

20 Claims, 5 Drawing Sheets

(56) References Cited

U.S. PATENT DOCUMENTS

2005/0192709 A1\* 9/2005 Danz ................... A61B 6/035
　　　　　　　　　　　　　　　　　　700/279
2009/0266160 A1　10/2009 Jeffrey et al.
2014/0074412 A1\* 3/2014 Busch ................. G01B 11/272
　　　　　　　　　　　　　　　　　　702/56

\* cited by examiner

SYSTEMS AND METHODS FOR IMBALANCE MEASUREMENT OF ROTATING MACHINERY

BACKGROUND OF THE INVENTION

The subject matter disclosed herein relates generally to systems and methods for determining balance of a rotating member, for example to systems and methods for determining balance of a rotating computed tomography (CT) gantry.

In CT imaging, an X-ray source may be rotated around an object to obtain imaging information. X-rays from the source attenuated by the object may be collected or detected by a detector and used to reconstruct an image.

The X-ray source may be mounted to a rotating gantry. An imbalance in the rotating gantry may adversely affect system reliability and/or performance. For example, if a CT gantry is not sufficiently well balanced, the iso-center of the gantry may experience a motion sufficient to cause artifacts in reconstructed images. However, the actual amount of movement that may cause such artifacts is small and difficult to measure. Currently employed approaches, such as the use of velocity probes, may be susceptible to damage, and/or be more expensive than desired.

BRIEF DESCRIPTION OF THE INVENTION

In one embodiment, a balancing system for use with a rotating member disposed in a stationary housing is provided. The balancing system is configured for mounting to the stationary housing, and includes a first inclinometer and at least one processor. The first inclinometer is configured to provide inclination information at a first frequency, and to provide vibration information at a second frequency. The second frequency is higher than the first frequency. The at least one processor is operably coupled to the first inclinometer to acquire the vibration information. The at least one processor is configured to determine a state of balance of the rotating member using the vibration information but not the inclination information.

In another embodiment, an imaging system is provided that includes a stationary housing, a rotating gantry, a computed tomography (CT) acquisition unit, a first inclinometer, and at least one processor. The rotating gantry is rotatably mounted to the stationary housing. The CT acquisition unit is mounted to the rotating gantry. The CT acquisition unit includes an X-ray source and a CT detector configured to collect CT imaging data of an object to be imaged, with the X-ray source and CT detector mounted to the rotating gantry. The first inclinometer is mounted to the stationary housing, and is configured to provide inclination information at a first frequency and vibration information at a second frequency. The second frequency is higher than the first frequency. The at least one processor is operably coupled to the first inclinometer and configured to acquire the vibration information from the first inclinometer. The at least one processor is configured to determine a state of balance of the rotating gantry using the vibration information but not the inclination information.

In another embodiment, a method is provided that includes rotating a rotating member coupled to a stationary housing. The method also includes transmitting at least one output signal from at least one inclinometer mounted to the stationary housing. The output signal includes inclination information and vibration information, with the inclination information at a lower frequency than the vibration information. Further, the method includes acquiring, with at least one processor, the vibration information. The method also includes determining, with the at least one processor, a state of balance of the rotating member using the vibration information but not the inclination information.

DETAILED DESCRIPTION OF THE INVENTION

Figure 1:
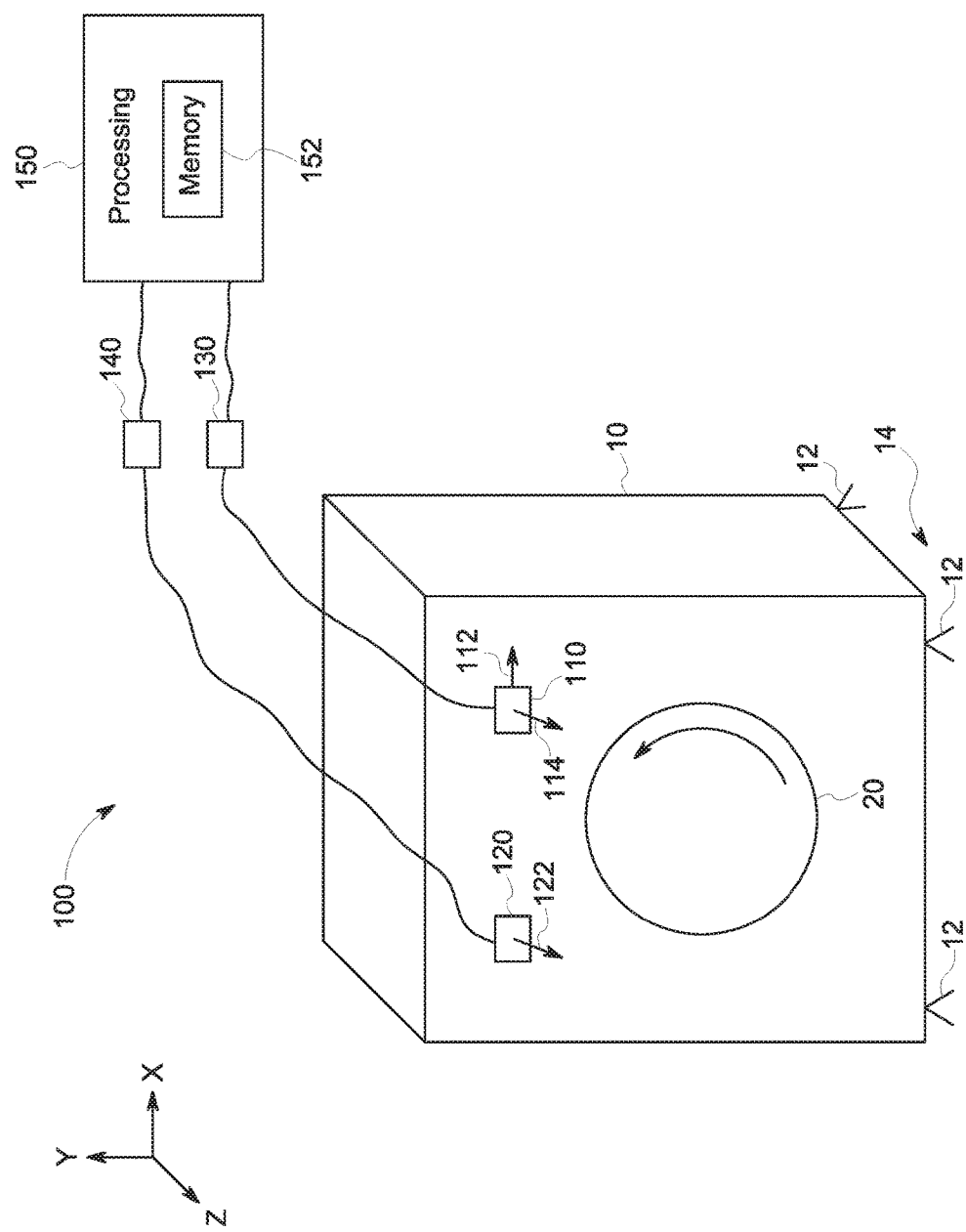
FIG. 1 is a schematic block diagram illustrating a balancing system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should be further understood that the figures illustrate example embodiments of the present disclosure. Variations, such as replacing or modifying one or more functional blocks, are possible to achieve similar results.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also used herein, the phrase "reconstructing an image" is not intended to exclude embodiments in which data representing an image is generated, but a viewable image is not. As used herein, the term "image" broadly refers to both viewable images and data representing a viewable image. It may be noted that various embodiments generate, or are configured to generate, at least one viewable image.

Various embodiments provide systems and methods for the measurement or determination of balance in a system with a rotating member, for example a CT imaging system including a rotating gantry. Various embodiments use an inclinometer (e.g., an accelerometer limited to low frequencies by a mechanical configuration such as inclusion of a dampening gas) mounted to a stationary member to which a rotating member is coupled. The low frequency limit of such inclinometers helps make such sensors well suited to measure the imbalance of CT gantries due to the limits on the maximum rotational speed of CT gantries. Various embodiments use information from relatively higher frequencies of an inclinometer (which are considerable lower than frequencies of conventional accelerometers) while disregarding lower frequency information that corresponds to inclination instead of vibration. As such, various embodiments utilize at least one inclinometer contrary to normal usage of an inclinometer, which typically involves utilizing lower frequency information to determine an inclination and disregarding higher, vibration-related, frequencies. Various embodiments accurately, reliably, and conveniently detect small enough vibrations to determine and/or finely tune the balance of a rotating member such as a CT gantry.

Various embodiments provide improved balance detection or determination of rotating members. A technical effect of at least one embodiment includes reduction of cost of balance detection. A technical effect of at least one embodiment includes improvement in the robustness, reliability, and/or convenience of balance detection. A technical effect of at least one embodiment includes providing elimination or reduction of recurring artifacts caused by imbalance of a rotating CT gantry.

FIG. 1 illustrates a balancing system 100 in accordance with an embodiment. The balancing system 100 may be utilized to sense, detect, or measure the balance (or imbalance) of a system including a rotating member, structure, or assembly. In the illustrated embodiment, the balancing system 100 is configured for use with a rotating member 20. The rotating member 20 is disposed in a stationary housing 10. For example, in some embodiments, the rotating member 20 may be a gantry of a medical imaging system configured to rotate about an object being imaged. As another example, the rotating member 20 may be a wind turbine in various embodiments. In the illustrated embodiment, the stationary housing 10 is mounted to a ground surface or floor 14 with mounts 12. The mounts 12 are configured as anchors that secure the stationary housing 10 to the floor 14. As the rotating member 20 rotates within the stationary housing 10, if the rotating member 20 is out of balance, vibrations from the rotating member 20 will be transmitted to the stationary housing 10, resulting in vibration of the stationary housing 10.

The vibration, or lack thereof, (and correspondingly, the balance of the stationary member 10 and rotating member 20) of the stationary housing 10 in the illustrated embodiment may be measured or determined with the balancing system 100. The balancing system 100 in the illustrated embodiment is configured for mounting to the stationary housing 10. All or a portion of the balancing system 100 may be mounted to the stationary housing 10. Generally, in various embodiments, the balancing system 100 is configured to use one or more inclinometers to provide vibration information to the processing unit 150 which determines a state of balance of the rotating member 20. In some embodiments, the processing unit 150 may only receive a portion of an output signal (or signals) from one or more inclinometers at a relatively higher frequency (information corresponding to vibration) and not receive information at a relatively lower frequency (information corresponding to inclination), such as at or near 0 Hertz from the one or more inclinometers, and the processing unit 150 accordingly may be understood as being AC coupled to the one or more inclinometers.

The depicted balancing system 100 includes a first inclinometer 110 and a processing unit 150. The first inclinometer 110 (and/or other inclinometers discussed herein) is configured to provide inclination information at a first frequency, and vibration information at a second frequency, with the second frequency higher than the first frequency. It may be noted that the first frequency and/or second frequency may include a range of frequencies. The first frequency may include a range that is adjacent to a range of the second frequency (e.g., the first frequency including a range of 0-1 Hertz and the second frequency including a range of 1-5 Hertz), or the first frequency may include a range that is spaced a distance or gap from a range of the second frequency (e.g., the first frequency including a range of 0-0.5 Hertz and the second frequency including a range of 1-5 Hertz). The portion of an output signal from the first inclinometer 110 corresponding to the first frequency may be used to determine an inclination (e.g., with respect to Earth's gravitational field), while the portion of an output signal from the first inclinometer 110 corresponding to the second frequency may be used to determine a vibration (or corresponding imbalance or state of balance).

The first inclinometer 110 is an example of a balancing sensor. Other balancing sensors may be employed additionally or alternatively in various embodiments. The first inclinometer 110 (and/or other inclinometers discussed herein) in various embodiments may be a Micro-Electro-Mechanical System (MEMS) based accelerometer that includes a mechanical configuration, such as inclusion of a dampening gas, configured to limit the frequency output of the MEMS based accelerometer. An example of a MEMS based inclinometer is the Murata SCA103T differential inclinometer series. The first inclinometer 110 (and/or other inclinometers discussed herein) may include a cantilevered mass and spring, with the mass disposed between plates and causing a measurable change in capacitance between the two plates as the mass vibrates. The mass and spring of the first inclinometer 110 may be vibrated below a resonant frequency in various embodiments. The first inclinometer 110

(and/or other inclinometers discussed herein) may be mounted to the stationary housing 10 as far as practicable from the mounts 12 (or otherwise positioned on a portion of the stationary housing 10 that will vibrate the most when subject to a vibration from the rotating member 20), for example, to improve the signal to noise ratio of an output generated responsive to the vibration.

In various embodiments, the first inclinometer 110 may have one or more axes of sensitivity. For example, the first inclinometer 110 may have one axis of sensitivity that corresponds to a static vibration (or corresponding state of balance) and a second axis of sensitivity that corresponds to a dynamic vibration (or corresponding state of balance). The first and second axes may be perpendicular to each other. For example, as seen in FIG. 1, the first inclinometer 110 may have a first axis of sensitivity 112 that corresponds to an x-direction and a second axes of sensitivity 114 that corresponds to a z-direction. Accordingly, the depicted first inclinometer 110 may be understood as having plural axes of sensitivity. Additionally or alternatively, as discussed herein, the first inclinometer 110 may have only one axis of sensitivity and/or one or more additional inclinometers may be utilized.

The depicted processing unit 150 is operably coupled to the first inclinometer 110, and is configured to acquire the vibration information from the first inclinometer 110. Also, the processing unit 150 is configured to determine a state of balance of the rotating member 20 using the vibration information, but not the inclination information. For example, the processing unit 150 may receive the inclination information, but discard or disregard the inclination information. As another example, the balancing system 100 may be configured to prevent all or a portion of the inclination information from being provided to the processing unit 150. For example, a filter or filters may be interposed between the processing unit 150 and the first inclinometer 110 and utilized to remove the inclination information from a signal provided from the first inclinometer 110 to the processing unit 150. The processing unit 150 may determine the state of balance based on or using a predetermined relationship or correlation between information received via one or more output signals from one or more inclinometers to the state of balance. The predetermined relationship may be stored and/or expressed in a formula, look-up table, or the like. Accordingly, based on vibration information received from one or more inclinometers (e.g., based on a portion of the output signal(s) from one or more inclinometers corresponding to vibration instead of inclination), the processing unit 150 may determine whether the rotating member 20 is in an acceptable state of balance, how the rotating member 20 is deviating from an acceptable state of balance (if not in balance), and/or how to mitigate or correct an imbalance (e.g., by specifying an amount and location of masses to be mounted to the rotating member 20).

For example, during a manufacture, inspection, or installation stage of the rotating member 20 (e.g., with the rotating member 20 coupled to the stationary housing 10) or comparable or equivalent rotating member, known imbalances may be applied to the rotating member, such as by adding mass in a predetermined amount at one or more predetermined locations of the rotating member. Then, with one or more inclinometers mounted to the stationary housing, the outputs from the one or more inclinometers generated responsive to a known rotation (e.g., at a given rotational speed) of the rotating member with the known imbalances applied may be recorded. By using a series of different amounts and/or locations of applied imbalances, a relationship between the inclinometer output and particular imbalances may be defined. A state of balance as used herein may refer to whether or not a rotating member is perfectly balanced (or within a tolerable margin of perfect balance). In some embodiments, the state of balance may also include an identification of where or how much the rotating member deviates from perfect balance and/or a configuration (e.g., amount and location of placement) of corrective masses to be applied to the rotating member to put the rotating member in a state of perfect balance (or within a tolerable margin).

In various embodiments, the processing unit 150 includes processing circuitry configured to perform one or more tasks, functions, or steps discussed herein. It may be noted that "processing unit" as used herein is not intended to necessarily be limited to a single processor or computer. For example, the processing unit 150 may include multiple processors and/or computers, which may be integrated in a common housing or unit, or which may be distributed among various units or housings. All or a portion of the processing unit 150 may be mounted on the stationary housing 10 in various embodiments, while in other embodiments the processing unit 150 may be separately housed or mounted from the stationary housing 10. It may be noted that operations performed by the processing unit 150 (e.g., operations corresponding to process flows or methods discussed herein, or aspects thereof) may be sufficiently complex that the operations may not be performed by a human being within a reasonable time period. For example, the analysis of signals from the inclinometers and/or determination of a state of balance may not be performed by a human being within a reasonable time period. The memory 152 may include one or more computer readable storage media. The memory 152 for example, may store acquired and/or processed signals received from one or more inclinometers or other balance sensors, correlations or relationships between signals received from inclinometers and states of balance of the rotating member 20, or the like. Further, the process flows and/or flowcharts discussed herein (or aspects thereof) may represent one or more sets of instructions that are stored in the memory 152 for direction of operations of the balancing system 100.

It may be noted that, in some embodiments, more than one inclinometer may be employed. For example, in the embodiment depicted in FIG. 1, in addition to the first inclinometer 110 that provides inclination information at a first frequency and vibration information at a second frequency, the balancing system 100 includes a second inclinometer 120. In various embodiments, the second inclinometer 120 may have an axis of sensitivity that differs from an axis of sensitivity of the first inclinometer 110. The second inclinometer 120 may be generally similar to the first inclinometer 110 in various respects. In the illustrated embodiment, the second inclinometer 120 is configured to provide second inclination information at a third frequency and second vibration information at a fourth frequency. The fourth frequency is higher than the third frequency. The fourth frequency of the second inclinometer 120 may be the same as the second frequency of the first inclinometer 110, and the third frequency of the second inclinometer 120 may be the same as the first frequency of the first inclinometer 110. The depicted second inclinometer 120 has an axis of sensitivity 122 (aligned in the z-direction in FIG. 2). When the second inclinometer 120 is used in conjunction with the first inclinometer 110 in various embodiments, the second inclinometer 120 may provide information measured with respect to the axis of sensitivity 122 while the first inclinometer 110 is used to obtain information along the axis of sensitivity 112.

Thus, the first inclinometer 110 and the second inclinometer 120 may be used to provide information for different axes of sensitivity (e.g., axes that are perpendicular to each other). It may be noted that in various embodiments, plural first inclinometers 110 (or inclinometers having a common first axis of sensitivity) may be utilized. Further, plural first inclinometers 110 (or inclinometers having a common first axis of sensitivity) may be utilized in conjunction with plural second inclinometers 120 (or inclinometers having a common second axis of sensitivity that is different than the common first axis of sensitivity of the plural first inclinometers 110).

As indicated herein, one or more high pass filters may be employed to remove the lower frequency inclination information while allowing the relatively higher frequency vibration information to pass through. In the illustrated embodiment, for example, the balancing system 100 includes a first high-pass filter 130 interposed between the first inclinometer 110 and the processing unit 150. The first high-pass filter 130 is configured to allow the vibration information (e.g., the information at the second, higher frequency) to pass from the first inclinometer 110 to the processing unit 150, and to prevent the passage of the inclination information (e.g., the information at the first, lower frequency) to pass from the first inclinometer 110 to the processing unit 150. In some embodiments, the second frequency (the frequency allowed to pass to the processing unit 150 or the frequency of information used by the processing unit to determine the state of balance) may include a range that includes at least one frequency at 1 Hz or above. For example, the second frequency may include a range of 1-3 Hertz. In some embodiments the second frequency may include a range that includes at least one frequency at 3 Hertz or above. For example, the second frequency may include a range of 3-5 Hertz. As another example, the first frequency may include a range of 0.5 Hertz and below.

The depicted balancing system 100 includes a second high-pass filter 140 interposed between the second inclinometer 120 and the processing unit 150. The second high-pass filter 140 is configured to allow the vibration information (e.g., the information at the fourth, higher frequency) to pass from the second inclinometer 120 to the processing unit 150, and to prevent the passage of the inclination information (e.g., the information at the third, lower frequency) to pass from the second inclinometer 120 to the processing unit 150. In some embodiments, the fourth frequency (the frequency allowed to pass to the processing unit 150 or the frequency of information used by the processing unit to determine the state of balance) may include a range that includes at least one frequency at 1 Hertz or above. For example, the fourth frequency may include a range of 1-3 Hertz, or as another example 3-5 Hertz. As another example, the third frequency may include a range of 0.5 Hertz and below.

Figure 2:
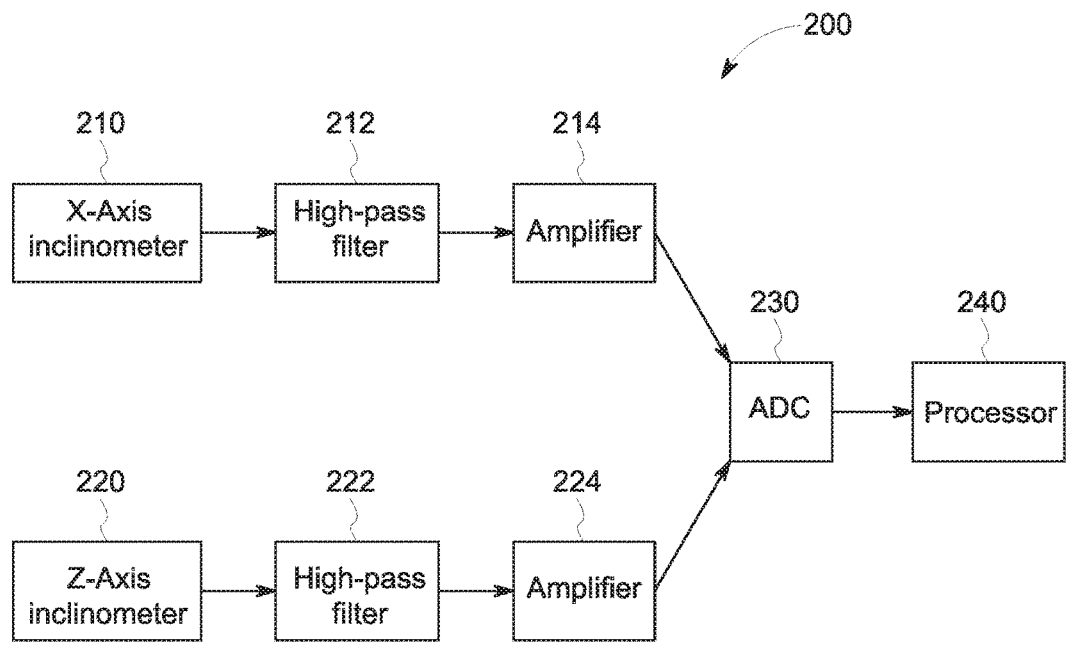
FIG. 2 illustrates a block diagram of a balancing system in accordance with various embodiments.

FIG. 2 provides a schematic block diagram of a balancing system 200 in accordance with an embodiment. The balancing system 200 is an example of a system utilizing two different inclinometers having two different axes of sensitivity, namely a first inclinometer 210 (having an x-axis of sensitivity) and a second inclinometer 220 (having a z-axis of sensitivity). The first inclinometer 210 and second inclinometer 220 provide output signals to a processor 240 via an analog-to-digital converter (ADC) 230. The signal from the first inclinometer 210, before reception by the ADC 230, is passed through a first high-pass filter 212 and a first amplifier 214. The first high-pass filter 212 is configured to allow vibration information at a relatively higher frequency to pass to the processor 240 and to prevent inclination information at a relatively lower frequency from passage to the processor 240 from the first inclinometer 210. Similarly, the signal from the second inclinometer 220, before reception by the ADC 230, is passed through a second high-pass filter 222 and a second amplifier 224. The second high-pass filter 222 is configured to allow vibration information at a relatively higher frequency to pass to the processor 240 and to prevent inclination information at a relatively lower frequency from passage to the processor 240 from the second inclinometer 220. It may be noted that, while various examples discussed herein include one or more amplifiers, in various embodiments an ADC may be able to read the signal from an inclinometer without an amplifier and achieve sufficient resolution for balancing.

The processor 240 utilizes the vibration information to determine a state of balance of a rotating member associated with the first inclinometer 210 and the second inclinometer 220. It may be noted that, in some embodiments, plural first and second inclinometers may be employed, with the block for the first inclinometer 210 representing plural inclinometers and the block for the first high-pass filter 212 representing corresponding plural filters; the block for the second inclinometer 220 representing plural inclinometers and the block for the second high-pass filter 222 representing corresponding plural filters; and the blocks for the first amplifier 214 and second amplifier 224 each representing one or more amplifiers. It may be noted also that, in other embodiments, the second inclinometer 220, second high-pass filter 222, and second amplifier 224 may be omitted, with the block for the first inclinometer 210 representing a multi-axis (e.g., x-axis and z-axis) inclinometer, the block for the first high-pass filter 212 representing plural corresponding filters (e.g., one filter for an x-axis signal and one filter for a z-axis signal), and the block for the first amplifier 214 representing one or more amplifiers. Further still, it may also be noted that in some embodiments plural multi-axis inclinometers may be employed, with the block for the first inclinometer 210 representing multiple multi-axis inclinometers.

Figure 3:
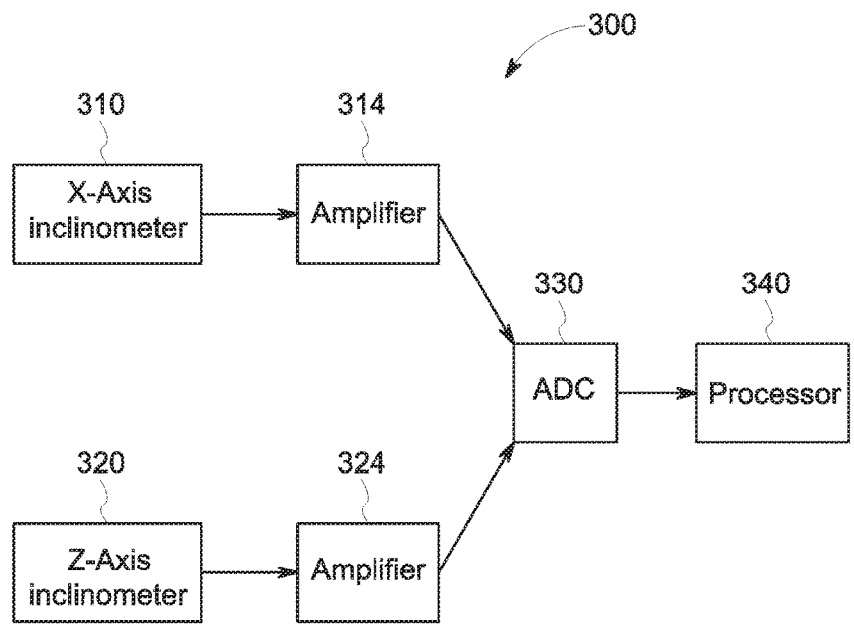
FIG. 3 illustrates a block diagram of a balancing system in accordance with various embodiments.

It may be noted that, in some embodiments, filters may not be utilized to separate the inclination information from the vibration information. For example, digital signal processing (DSP) in a processor may be utilized to provide high-pass filtration to isolate the vibration information for use in determining a state of balance. FIG. 3 provides a schematic block diagram of a balancing system 300 in accordance with an embodiment. The balancing system 300 is an example of a system that does not employ filters before reception of inclinometer outputs by an ADC and/or processor. The balancing system 300 includes two different inclinometers having two different axes of sensitivity, namely a first inclinometer 310 (having an x-axis of sensitivity) and a second inclinometer 320 (having a z-axis of sensitivity). The first inclinometer 310 and second inclinometer 320 provide output signals to a processor 340 via an analog-to-digital converter (ADC) 330. The signal from the first inclinometer 310, before reception by the ADC 330, is passed through a first amplifier 314. Similarly, the signal from the second inclinometer 320, before reception by the ADC 330, is passed through a second amplifier 324. The processor 340, which may employ digital signal processing to discard a low frequency portion of a received signal corresponding to inclination information, utilizes the vibration information to determine a state of balance of a rotating member associated with the first inclinometer 310 and the second inclinometer 320.

Figure 4:
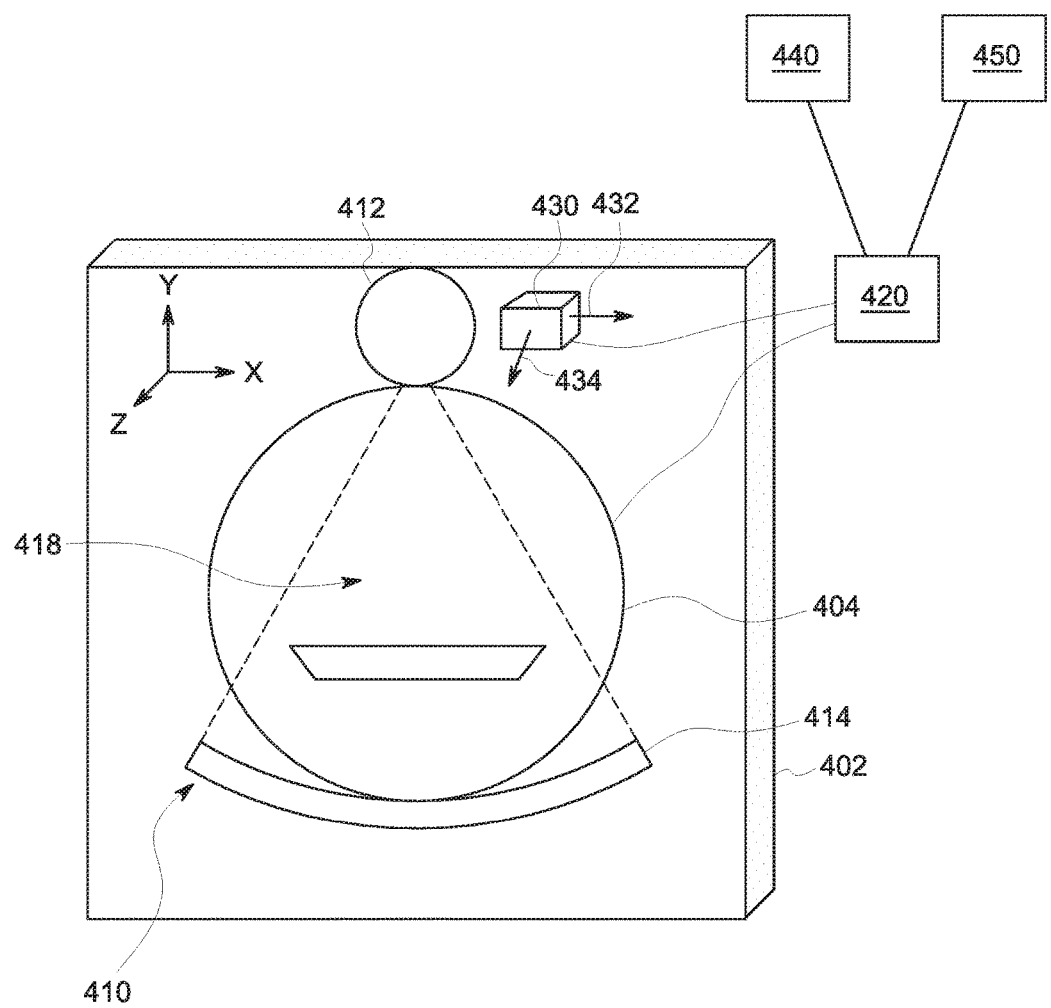
FIG. 4 is a schematic block diagram illustrating an imaging system in accordance with various embodiments.

In various embodiments, a balancing system as discussed herein may be utilized in conjunction with or as a part of a medical imaging system, such as a computed tomography (CT) imaging system. FIG. 4 depicts a schematic view of an imaging system 400 formed in accordance with various embodiments.

The imaging system 400 may be configured, for example, to perform computed tomography (CT) scanning of an object, such as a human or animal patient (or portion thereof), such as CT scanning for a perfusion study. The imaging system 400 includes a stationary housing 402 and a rotating gantry 404 mounted to the stationary housing 402. The imaging system 400 includes a CT acquisition unit 410 and a processing unit 420. The CT acquisition unit 410 is mounted to or forms a portion of the rotating gantry 404. Generally, the CT acquisition unit 410 is configured to acquire projection data or imaging data (e.g., CT data or CT imaging information), and the processing unit 420 is configured to reconstruct images using the data acquired by the CT acquisition unit 410. The imaging system 400 also includes an inclinometer 430. In the depicted embodiment, the inclinometer 430 has a first axis of sensitivity 432 in the x-direction and a second axis of sensitivity 434 in the y-direction. The inclinometer 430 is operably coupled to the processing unit 420, and provides an output signal to the processing unit 420. The inclinometer 430 and processing unit 420 may be generally similar in various respects to corresponding aspects of embodiments discussed herein (e.g., in connection with FIGS. 1-3). Generally, vibration information from the inclinometer 430 is used by the processing unit 420 to determine a state of balance of the rotating gantry 404. It may be noted that various embodiments may include additional components, or may not include all of the components shown in FIG. 4 (for example, various embodiments may provide sub-systems for use with other sub-systems to provide an imaging system). Further, it may be noted that certain aspects of the imaging system 400 shown as separate blocks in FIG. 4 may be incorporated into a single physical entity, and/or aspects shown as a single block in FIG. 4 may be shared or divided among two or more physical entities. It may also be noted that the imaging system 400 may incorporate aspects of the balancing systems discussed in connection with FIGS. 1-3. For example, first and second inclinometers having different axes of sensitivity may be employed in various embodiments.

The depicted CT acquisition unit 410 includes an X-ray source 412 and a CT detector 414. (For additional information regarding example CT systems, see FIG. 6 and related discussion herein.) The X-ray source 412 and the CT detector 414 (along with associated components such as bowtie filters, source collimators, detector collimators, or the like (not shown in FIG. 4)) may rotate relative to the object to be imaged. For example, in some embodiments, the X-ray source 412 and the CT detector 414 may rotate about a central axis of a bore of the rotating gantry 404.

Generally, X-rays from the X-ray source 412 may be guided to an object 402 to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter may be configured to absorb radiation from the X-ray source 412 to control distribution of X-rays passed to the object to be imaged.

X-rays that pass through the object to be imaged are attenuated by the object and received by the CT detector 414 (which may have a detector collimator associated therewith), which detects the attenuated X-rays and provides imaging information to the processing unit 420. The processing unit 420 may then reconstruct an image of the scanned portion of the object 402 using the imaging information (or projection information) provided by the CT detector 414. The processing unit 420 may include or be operably coupled to the output unit 440, which in the illustrated embodiment is configured to display an image, for example, an image reconstructed by the processing unit 420 using imaging information from the CT detector 414. The depicted input unit 450 is configured to obtain input corresponding to a scan to be performed, with the processing unit 420 using the input to determine one or more scan settings (e.g., tube voltage, tube current, scanning rotation speed, or the like). The input unit 450 may include a keyboard, mouse, touchscreen or the like to receive input from an operator, and/or may include a port or other connectivity device to receive input from a computer or other source.

In the illustrated embodiment, the X-ray source 412 is configured to rotate about an object to be imaged. For example, the X-ray source 412 and the CT detector 414 may be positioned about a bore 418 of the gantry 404 and rotated about the object to be imaged. As the X-ray source 412 rotates about the object during an imaging scan, X-rays received by the CT detector 414 during one complete rotation provide a 360 degree view of X-rays that have passed through the object. Other imaging scanning ranges may be used in alternative embodiments. The CT imaging information may be collected as a series of views that together make up a rotation or portion thereof.

The depicted processing unit 420 is operably coupled to the input unit 450, the output unit 440, and the CT acquisition unit 410. As indicated herein, the processing unit 420 is configured to control various aspects of the acquisition unit and/or to reconstruct an image using information obtained via the acquisition units. For example, the processing unit 420 may be configured to reconstruct a CT image using information collected by the CT acquisition unit 410. The processing unit 420 acquires vibration information from the inclinometer 430, and uses the vibration information to determine a state of balance of the gantry 404. In some embodiments, lower frequency inclination information may be filtered out of an output signal from the inclinometer 430 before reception by the processing unit 420. Additionally or alternatively, the processing unit 420 may filter out or otherwise remove, discard, or disregard lower frequency inclination information received by the processing unit 420 from the inclinometer 430.

Figure 5:
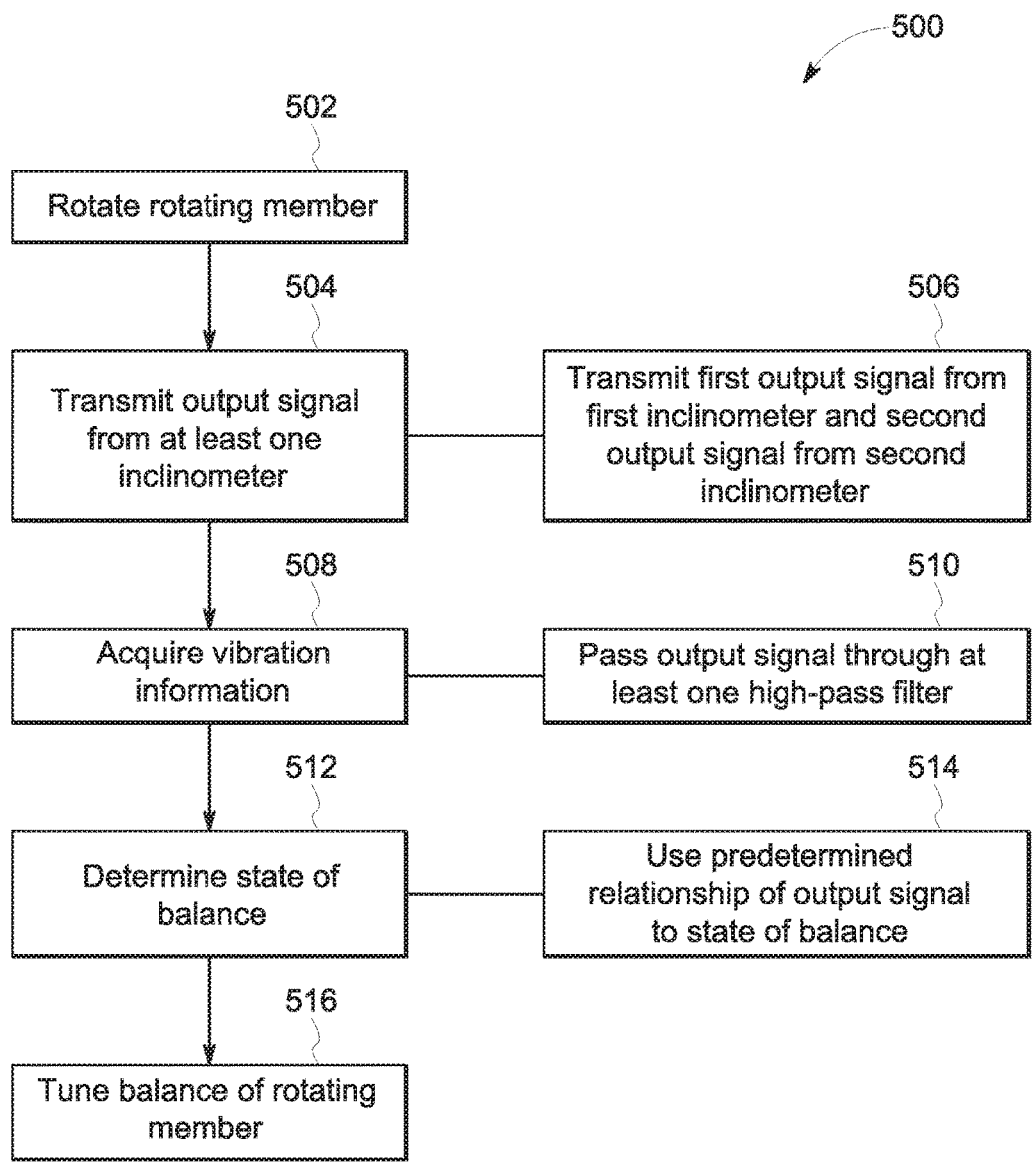
FIG. 5 is a flowchart of a method in accordance with various embodiments.

FIG. 5 provides a flowchart of a method 500 for determining a state of balance for rotating member, in accordance with various embodiments. The method 500, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware (e.g., one or more aspects of the processing unit 150) to perform one or more operations described herein.

At 502, a rotating member is rotated. The rotating member is mounted or coupled to a stationary housing, and rotates with respect to the stationary housing. The rotating member, for example, may be a CT acquisition unit. As another example, the rotating member may be a wind turbine. Various embodiments may be utilized in connection with rotating members that rotate fairly slowly, for example, 300 revolutions per minute (RPM) or less. For example, in some embodiments, a CT acquisition unit may rotate at about 30 RPM. The relatively slow rotational speeds, combined with the structural characteristics and inertia of the stationary housing may generate relatively low forces or accelerations in the stationary housing responsive to the rotation of the rotating member. For example, to determine a state of balance of the rotating member, it may be necessary or desirable to measure amounts of acceleration of 3 milliG's or less, with necessary or desired resolution in the microG range, in the stationary housing. As conventional measurement techniques (e.g., accelerometers) may not provide the desired resolution or be appropriate for use with such small accelerations, in various embodiments vibrational information from an inclinometer may be employed to determine a state of balance as discussed herein.

At 504, an output signal is transmitted from at least one inclinometer mounted to the stationary housing. The at least one inclinometer is an example of a balance sensor mounted to the stationary housing. Other types of balancing sensors may be employed additionally or alternatively in various embodiments. The output signal in various embodiments includes inclination information corresponding to the orientation of the stationary housing with respect to a gravitational field, and vibration information corresponding to a vibration occurring in the stationary housing responsive to rotation of the rotating member. The inclination information may be included in or correspond to a portion of the output signal at a relatively lower frequency (e.g., at or near zero Hertz), while the vibration information may be included in or correspond to a portion of the output signal at a relatively higher frequency (e.g., at or near 3 Hertz). The at least one inclinometer may include, for example, one or more MEMS based accelerometers that have been provided with a dampening gas that limits the frequency output of the MEMS based accelerometer.

It may be noted that in some embodiments, the inclinometer may have more than one axes of sensitivity. Also, in some embodiments, the inclinometer may have a single axis of sensitivity, and one or more additional inclinometers may be employed. For example, in the depicted embodiment, at 506, a first output signal is transmitted from a first inclinometer and a second output signal is transmitted from a second inclinometer. The first inclinometer has a first axis of sensitivity, and the second output signal has a second axis of sensitivity that is different from the first axis of sensitivity. The second axis may be perpendicular to the first axis. For example, one axis of sensitivity may be oriented in an x-direction and the other oriented in a z-direction.

At 508, vibration information from the at least one inclinometer is acquired by at least one processor (e.g., processing unit 150). In some embodiments, the at least one processor may acquire or receive both the inclination information and the vibration information, but discard or otherwise disregard the inclination information. In some embodiments, the at least one processor may only receive the vibration information. For example, in the illustrated embodiment, at 510, the output signal (or signals) from the at least one inclinometer is passed through at least one high-pass filter to remove the inclination information and to provide a vibration signal to the at least one processor. In some embodiments, the at least one high-pass filter may be configured to provide a vibration signal to the at least one processor that removes lower frequency information but includes a range of frequencies including at least one frequency above 1 Hertz. In some embodiments, the at least one high-pass filter may be configured to provide a vibration signal to the at least one processor that removes lower frequency information but includes a range of frequencies including at least one frequency above 3 Hertz.

At 512, a state of balance of the rotating member is determined using the vibration information from the at least one transmitted output signal, but not the inclination information. For example, the inclination information may be filtered out or otherwise removed or disregarded. The determined state of balance may indicate one or more of whether or not the rotating member is in balance (or within a predetermined tolerance of being in balance), an amount or measure of how far out of balance the rotating member is, or an identification of a modification to the rotating member (e.g., one or more amounts and locations of masses that may be added to the rotating member) that will place the rotating member in balance (or within a predetermined tolerance of being in balance). In the illustrated embodiment, at 514, a predetermined relationship of the output signal to the state of balance is used to determine the state of balance. For example, known imbalances may be applied to a rotating member, and the output signals for each known imbalance correlated with the location(s) and amount(s) of mass(es) of the known imbalance. Then, a relationship between output signal and the location/amount of unbalancing masses may be defined, for example using curve-fitting and/or interpolation between known data points defined by known imbalances and corresponding inclinometer output signals (or aspects of output signals). The relationship may also correlate a correction to one or more output signals. For example, the correction may be determined based on the known imbalance that corresponds to a given output signal. It may be noted that, in some embodiments, the inclination information may be used for a purpose other than determining a state of balance. For example, an inclination angle of a system that tilts may be measured, or an accuracy of an installation leveling may be checked using inclination information.

At 516, the balance of the rotating member is tuned based on the determined state of balance. For example, with an output signal (or signals) correlated to a known imbalance identified, one or more masses may be mounted or otherwise added to (or subtracted from) the rotating gantry in an amount and location (or locations) to counteract the corresponding known imbalance. The balance of a rotating member may be determined and/or tuned at various different times, such as after manufacture or assembly, after installation, as part of a periodic calibration (e.g., daily), and/or in response to a change in use (e.g., type of scan performed) or configuration (e.g., addition, subtraction, or modification of a component) of the rotating member or a system including the rotating member.

Figure 6:
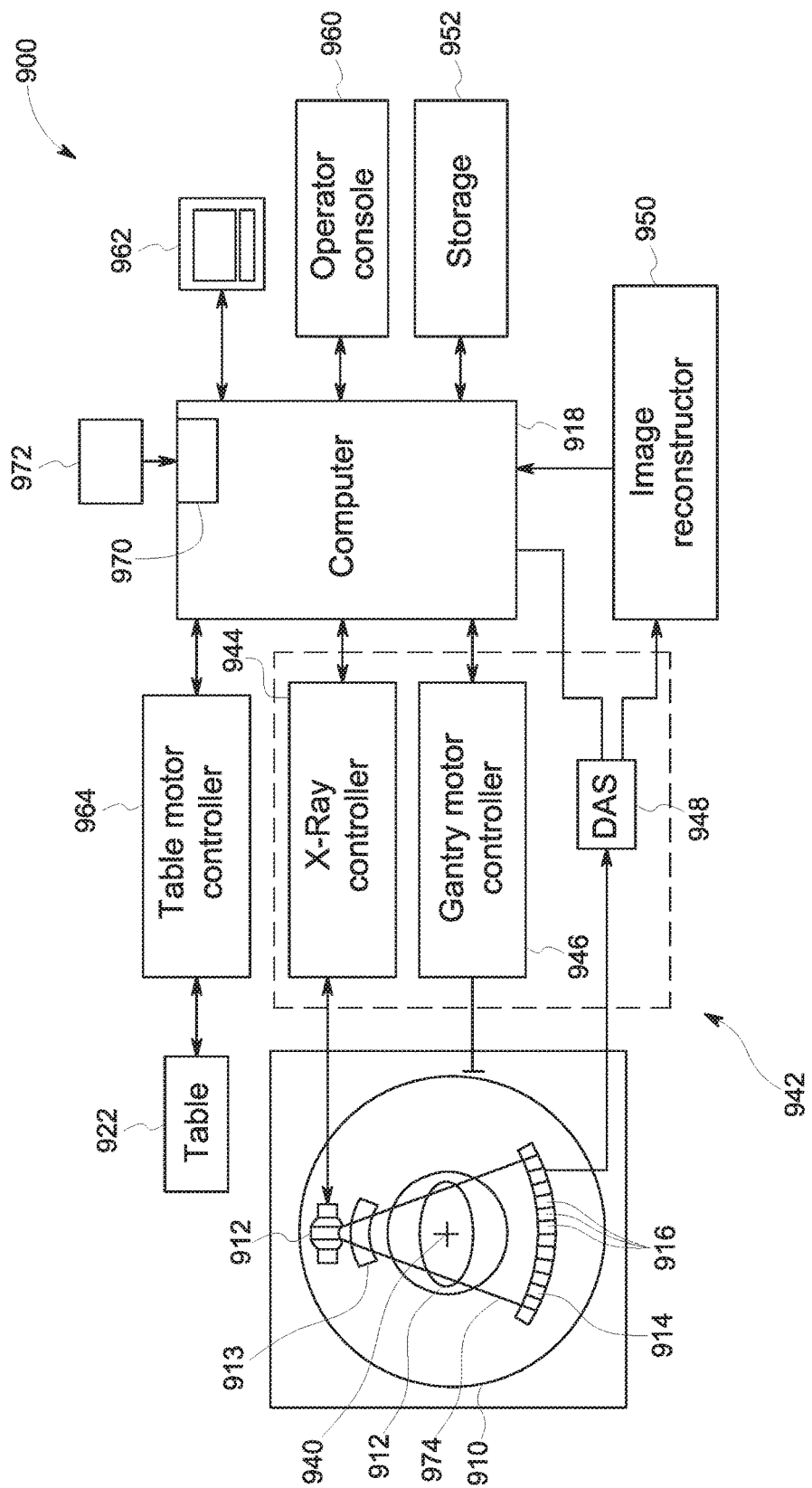
FIG. 6 is a schematic block diagram of an imaging system in accordance with various embodiments.

Various methods and/or systems (and/or aspects thereof) described herein may be implemented using a medical imaging system. For example, FIG. 6 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 150, or be operably coupled to one or more aspects of the processing unit 150. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 6 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A balancing system for use with a rotating member disposed in a stationary housing, the balancing system configured for mounting to the stationary housing, the balancing system comprising:
   a first inclinometer configured to provide inclination information at a first frequency and vibration information at a second frequency, the second frequency higher than the first frequency; and
   at least one processor operably coupled to the first inclinometer, the at least one processor coupled to the first inclinometer and configured to acquire the vibration information from the first inclinometer, the at least one processor configured to disregard the inclination information at the first frequency and to determine a state of balance of the rotating member using only the vibration information but not the inclination information.

2. The balancing system of claim 1, wherein the first inclinometer comprises a Micro-Electro-Mechanical System (MEMS) based accelerometer comprising a dampening gas configured to limit the frequency output of the accelerometer.

3. The balancing system of claim 1, further comprising a high-pass filter interposed between the first inclinometer and the at least one processor, the high-pass filter configured to allow the vibration information at the second frequency to pass to the at least one processor and to prevent the inclination information at the first frequency from passing to the at least one processor.

4. The balancing system of claim 3, wherein the second frequency comprises a range having a lower boundary at 1 Hertz or above.

5. The balancing system of claim 1, further comprising a second inclinometer configured to provide second inclination information at a third frequency and second vibration information at a fourth frequency, the fourth frequency higher than the second frequency, wherein the first inclinometer has a first axis of sensitivity and the second inclinometer has a second axis of sensitivity that is different than the first axis of sensitivity.

6. The balancing system of claim 5, wherein the system comprises plural inclinometers having the first axis of sensitivity and plural inclinometers having the second axis of sensitivity.

7. The balancing system of claim 1, wherein the first inclinometer comprises plural axes of sensitivity.

8. An imaging system comprising:
a stationary housing:
a rotating gantry rotatably mounted to the stationary housing;
a computed tomography (CT) acquisition unit mounted to the rotating gantry, the CT acquisition unit comprising an X-ray source and a CT detector configured to collect CT imaging data of an object to be imaged, the X-ray source and CT detector mounted to the rotating gantry; and
a first inclinometer mounted to the stationary housing, the first inclinometer configured to provide inclination information at a first frequency and vibration information at a second frequency, the second frequency higher than the first frequency; and
at least one processor operably coupled to the first inclinometer, the at least one processor coupled to the first inclinometer and configured to acquire the vibration information from the first inclinometer, the at least one processor configured to disregard the inclination information at the first frequency and to determine a state of balance of the rotating gantry using only the vibration information but not the inclination information.

9. The imaging system of claim 8, wherein the first inclinometer comprises a Micro-Electro-Mechanical System (MEMS) based accelerometer comprising a dampening gas configured to limit the frequency output of the accelerometer.

10. The imaging system of claim 8, further comprising a high-pass filter interposed between the first inclinometer and the at least one processor, the high-pass filter configured to allow the vibration information at the second frequency to pass to the at least one processor and to prevent the inclination information at the first frequency from passing to the at least one processor.

11. The imaging system of claim 10, wherein the second frequency comprises a range having a lower boundary at 1 Hertz or above.

12. The imaging system of claim 8, further comprising a second inclinometer configured to provide second inclination information at a third frequency and second vibration information at a fourth frequency, the fourth frequency higher than the third frequency, wherein the first inclinometer has a first axis of sensitivity and the second inclinometer has a second axis of sensitivity that is different than the first axis of sensitivity.

13. The imaging system of claim 12, wherein the system comprises plural inclinometers having the first axis of sensitivity and plural inclinometers having the second axis of sensitivity.

14. The imaging system of claim 8, wherein the first inclinometer comprises plural axes of sensitivity.

15. A method comprising:
rotating a rotating member coupled to a stationary housing;
transmitting at least one output signal from at least one inclinometer mounted to the stationary housing, the output signal comprising inclination information and vibration information, the inclination information at a lower frequency than the vibration information;
acquiring, with at least one processor, the vibration information, while disregarding the inclination information at the lower frequency than the vibration information; and
determining, with the at least one processor, a state of balance of the rotating member using only the vibration information but not the inclination information.

16. The method of claim 15, wherein determining the state of balance comprises using a predetermined relationship of the output signal to the state of balance determined using known imbalances.

17. The method of claim 15, wherein acquiring the vibration information comprises passing the at least one output signal through at least one high-pass filter configured to remove the inclination information to provide a vibration signal.

18. The method of claim 17, wherein the vibration signal allowed to pass from the at least one high-pass filter comprises a range having a lower boundary at 1 Hertz or above.

19. The method of claim 15, wherein transmitting the output signal comprises transmitting a first output signal from a first inclinometer having a first axis of sensitivity and transmitting a second output signal from a second inclinometer having a second axis of sensitivity different from the first axis of sensitivity.

20. The method of claim 15, wherein the at least one inclinometer comprises a Micro-Electro-Mechanical System (MEMS) based accelerometer comprising a dampening gas configured to limit the frequency output of the accelerometer.

* * * * *